United States Patent
Miller (10) Patent No.: US 9,266,239 B2
(45) Date of Patent: Feb. 23, 2016

(54) CONSTRAINT BASED CONTROL IN A MINIMALLY INVASIVE SURGICAL APPARATUS

(75) Inventor: Brian Miller, Lincoln, NE (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 1321 days.

(21) Appl. No.: 11/318,794

(22) Filed: Dec. 27, 2005

(65) Prior Publication Data

US 2007/0144298 A1    Jun. 28, 2007

(51) Int. Cl.
*A61B 19/00*    (2006.01)
*B25J 9/16*    (2006.01)

(52) U.S. Cl.
CPC .............. *B25J 9/1676* (2013.01); *A61B 19/22* (2013.01); *A61B 19/2203* (2013.01); *A61B 19/50* (2013.01); *A61B 19/5212* (2013.01); *A61B 19/56* (2013.01); *A61B 2019/2223* (2013.01); *A61B 2019/2292* (2013.01); *Y10T 74/20305* (2015.01)

(58) Field of Classification Search
CPC .................. A61B 19/2203; A61B 2019/2223; A61B 19/22; A61B 19/5244; A61B 2019/2296; A61B 2019/2276; A61B 2019/2211; A61B 2019/2249; A61B 2019/507; A61B 19/30; A61B 2019/5248; A61B 2019/2292; A61B 19/56; A61B 2019/223; A61B 19/50; B25J 9/1676
USPC ........................................................ 606/130
See application file for complete search history.

(56) References Cited

U.S. PATENT DOCUMENTS

| | | | |
|---|---|---|---|
| 5,299,288 A | 3/1994 | Glassman et al. | |
| 5,561,708 A | 10/1996 | Remillard | |
| 5,572,999 A * | 11/1996 | Funda et al. | 600/118 |
| 5,923,139 A | 7/1999 | Colgate et al. | |
| 6,057,833 A | 5/2000 | Heidmann et al. | |
| 6,204,620 B1 | 3/2001 | McGee et al. | |
| 6,493,608 B1 | 12/2002 | Niemeyer | |
| 6,642,686 B1 | 11/2003 | Ruch | |
| 6,843,793 B2 * | 1/2005 | Brock et al. | 606/130 |
| 6,864,886 B1 | 3/2005 | Cavallaro et al. | |
| 7,075,556 B1 | 7/2006 | Meier et al. | |
| 7,206,626 B2 * | 4/2007 | Quaid, III | 600/407 |
| 7,747,311 B2 | 6/2010 | Quaid et al. | |
| 7,831,292 B2 | 11/2010 | Quaid et al. | |

(Continued)

FOREIGN PATENT DOCUMENTS

GB    2298931 A    9/1996

OTHER PUBLICATIONS

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

(Continued)

*Primary Examiner* — Katherine M Shi
*Assistant Examiner* — Michael Mendoza (57) ABSTRACT

A medical robotic system that includes a robotically controlled surgical instrument. The system includes a constraint controller that constrains the movement of the instrument based on a predetermined parameter. The parameter may be a surgical space, wherein the instrument cannot be moved into, or alternatively cannot be moved out of, the space. The surgically constrained spaced may be defined through a telestrator screen that allows a surgeon to point and click the boundaries of the space.

19 Claims, 7 Drawing Sheets

(56) References Cited

U.S. PATENT DOCUMENTS

| | | | |
|---|---|---|---|
| 7,907,166 B2 | 3/2011 | Lamprecht et al. | |
| 8,073,528 B2 | 12/2011 | Zhao et al. | |
| 8,108,072 B2 | 1/2012 | Zhao et al. | |
| 8,147,503 B2 | 4/2012 | Zhao et al. | |
| 8,184,880 B2 | 5/2012 | Zhao et al. | |
| 8,398,541 B2 | 3/2013 | Dimaio et al. | |
| 8,543,240 B2 | 9/2013 | Itkowitz et al. | |
| 8,639,000 B2 | 1/2014 | Zhao et al. | |
| 2001/0001132 A1 | 5/2001 | Funda | |
| 2004/0024311 A1* | 2/2004 | Quaid, III | 600/428 |
| 2004/0034282 A1 | 2/2004 | Quaid | |
| 2004/0034302 A1 | 2/2004 | Abovitz et al. | |
| 2004/0070615 A1 | 4/2004 | Ewing et al. | |
| 2004/0115606 A1 | 6/2004 | Davies | |
| 2004/0128026 A1 | 7/2004 | Harris | |
| 2004/0243147 A1* | 12/2004 | Lipow | 606/130 |
| 2005/0125150 A1 | 6/2005 | Wang et al. | |
| 2005/0179702 A1 | 8/2005 | Tomlinson et al. | |
| 2006/0087504 A1 | 4/2006 | Meier et al. | |
| 2006/0258938 A1 | 11/2006 | Hoffman et al. | |
| 2007/0053589 A1* | 3/2007 | Gering | 382/173 |
| 2007/0167702 A1 | 7/2007 | Hasser et al. | |
| 2009/0046146 A1 | 2/2009 | Hoyt | |
| 2009/0248041 A1 | 10/2009 | Williams et al. | |
| 2010/0164950 A1 | 7/2010 | Zhao et al. | |
| 2011/0050852 A1 | 3/2011 | Lamprecht et al. | |
| 2011/0118752 A1 | 5/2011 | Itkowitz et al. | |
| 2012/0020547 A1 | 1/2012 | Zhao et al. | |
| 2012/0059391 A1 | 3/2012 | Diolaiti et al. | |
| 2012/0071891 A1 | 3/2012 | Itkowitz et al. | |
| 2012/0071892 A1 | 3/2012 | Itkowitz et al. | |
| 2012/0109152 A1 | 5/2012 | Quaid, III | |
| 2013/0245375 A1 | 9/2013 | Dimaio et al. | |

OTHER PUBLICATIONS

PCT/US06/62508 International Search Report and Written Opinion of the International Search Authority, mailed Feb. 12, 2008, 9 pages.

Adams II, John B., "Telesurgery in Urologic Disease," 1997, 4 pages.

Anderson R.J., "Autonomous, Teleoperated, and Shared Control of Robot Systems," Proceedings of the 1996 IEEE International Conference on Robotics and Automation, Apr. 1996, pp. 2025-2032.

Barbara, Santa, "Computers and Robotics in the Operating Room 2000," 1977, 88 pages.

Drasin, Todd and Carlos Gracia, "Using Telerobots as Assistant Surgeons," Chapter 26 in Primer of Robotic & Telerobotic Surgery, Eds. Garth H. Ballantyne et al., Pub. by Lippincott Williams & Wilkins, Philadelphia, 2004, pp. 188-195.

Herman, Barry C., et al, "Telerobotic surgery creates opportunity for augmented reality surgery," Abstract No. T1F2, Telemedicine Journal and E-Health, vol. 11, Issue 2, p. 203, Apr. 2005.

Intuitive Surgical, Inc., "Intuitive Surgical daVinci API v5.0 Reference Manual," generated Jul. 17, 2006, 149 pages.

Kim, Yoon Sang, "Surgical Telementoring Initiation of a Regional Telemedicine Network: Projection of Surgical Expertise in the WWAMI Region," 3rd 2008 International Conference on Convergence and Hybrid Information Technology (ICCIT 08), Nov. 11-13, 2008, Busan, Korea, vol. 1, pp. 974-979, IEEE.

Link, Richard E. et al., "Telesurgery: Remote Monitoring and Assistance During Laparoscopy," Urol Clin North Am, 2001, pp. 177-188, vol. 28—Issue 1, Sanders.

Micali, S. et al., "Feasibility of telementoring between Baltimore (USA) and Rome (Italy): the first five cases," J Endourol, 2000, pp. 493-496, vol. 14—Issue 6.

Moore, R.G. et al., "Telementoring of laparoscopic procedures: Initial clinical experience," Surgical Endoscopy, 1996, pp. 107-110, vol. 10—Issue 2, Springer-Verlag.

Rafiq A., et al., "Digital Video Capture and Synchronous Consultation in Open Surgery," Annals of Surgery, 2004, vol. 239 (4), pp. 567-573.

Rafiq, Azhar and Ronald C. Merrell, "SOCRATES: Telementoring for Telerobotics," Chapter 11 in Primer of Robotic & Telerobotic Surgery, Eds. Garth H. Ballantyne et al., Pub. by Lippincott Williams & Wilkins, Philadelphia, 2004, pp. 78-85.

Rafiq, Azhar et al., "SOCRATES: Telementoring for Telerobotics," and Todd Drasin et al., "Using Telerobots as Assistant Surgeons," Chapters 11 and 26: Primer of Robotic & Telerobotic Surgery, Garth H. Ballantyne et al., 2004, Ilppincott Williams & Wilkins, pp. 78-85 and 188-195.

Rosser, James C., "Yale School of Medicine—The Impact of Technology on Surgical Health Care Delivery in the Next Millennium," 1977, 10 pages.

Schulam Peter G. et al., "Telesurgical mentoring: Initial clinical Experience," Surgical Endoscopy, 1997, pp. 1001-1005, vol. 11, Springer-Verlag.

Stoianovici, Dan, "Robotic tools for minimally invasive urologic surgery," Chapter in Complications of Urologic Laparoscopic Surgery: Recognition, Management and Prevention, published 2005 by Taylor Francis, paper dated Dec. 2002, 17 pages.

Taylor, Russell H. and Dan Stoianovici, "Medical Robotic Systems in Computer-Integrated Surgery," Problems in General Surgery, by Lippincott Williams & Wilkins, Inc., Philadelphia, Pennsylvania. vol. 20, No. 2, pp. 1-9, 2003.

Lee, Benjamin R. et al., "A novel method of surgical instruction: international telementoring," World Journal of Urology, 1998, pp. 367-370, vol. 16—Issue 6, Springer Berlin / Heidelberg.

Lee C.H., et al., "Purification and Characterization of a Polysome-associated Endoribonuclease that Degrades c-myc mRNA in Vitro," The Journal of Biological Chemistry, 1998, vol. 273 (39), pp. 25261-25271.

* cited by examiner

CONSTRAINT BASED CONTROL IN A MINIMALLY INVASIVE SURGICAL APPARATUS

BACKGROUND OF THE INVENTION

1. Field of the Invention

The present invention relates to a medical robotic system.

2. Background Information

Blockage of a coronary artery may deprive the heart of blood and oxygen required to sustain life. The blockage may be removed with medication or by an angioplasty. For severe blockage a coronary artery bypass graft (CABG) is performed to bypass the blocked area of the artery. CABG procedures are typically performed by splitting the sternum and pulling open the chest cavity to provide access to the heart. An incision is made in the artery adjacent to the blocked area. The internal mammary artery is then severed and attached to the artery at the point of incision. The internal mammary artery bypasses the blocked area of the artery to again provide a full flow of blood to the heart. Splitting the sternum and opening the chest cavity can create a tremendous trauma to the patient. Additionally, the cracked sternum prolongs the recovery period of the patient.

Computer Motion of Goleta, Calif. provides a system under the trademark ZEUS that allows a surgeon to perform a minimally invasive CABG procedure. The procedure is performed with instruments that are inserted through small incisions in the patient's chest. The instruments are controlled by robotic arms. Movement of the robotic arms and actuation of instrument end effectors are controlled by the surgeon through a pair of handles and a foot pedal that are coupled to an electronic controller. Alternatively, the surgeon can control the movement of an endoscope used to view the internal organs of the patient through voice commands.

The handles and a screen are typically integrated into a console that is operated by the surgeon to control the various robotic arms and medical instruments of a ZEUS system. When performing surgery it is sometimes desirable to constrain the movement of the surgical instruments. For example, it may be desirable to prevent the instruments from making contact with a patient's organ, or it may be desirable to guide a biopic instrument along a predetermined path. It would also be desirable to allow a surgeon to readily define the constraints of the system.

BRIEF SUMMARY OF THE INVENTION

A medical system with a robotic arm that moves a surgical instrument. The system includes a constraint controller that constrains the movement of the surgical instrument based on a predetermined parameter.

DETAILED DESCRIPTION

Disclosed is a medical robotic system that includes a robotically controlled surgical instrument. The system includes a constraint controller that constrains the movement of the instrument based on a predetermined parameter. The parameter may be a surgical space, wherein the instrument cannot be moved into, or alternatively cannot be moved out of, the space. The surgically constrained spaced may be defined through a telestrator screen that allows a surgeon to point and click the boundaries of the space.

Figure 1:
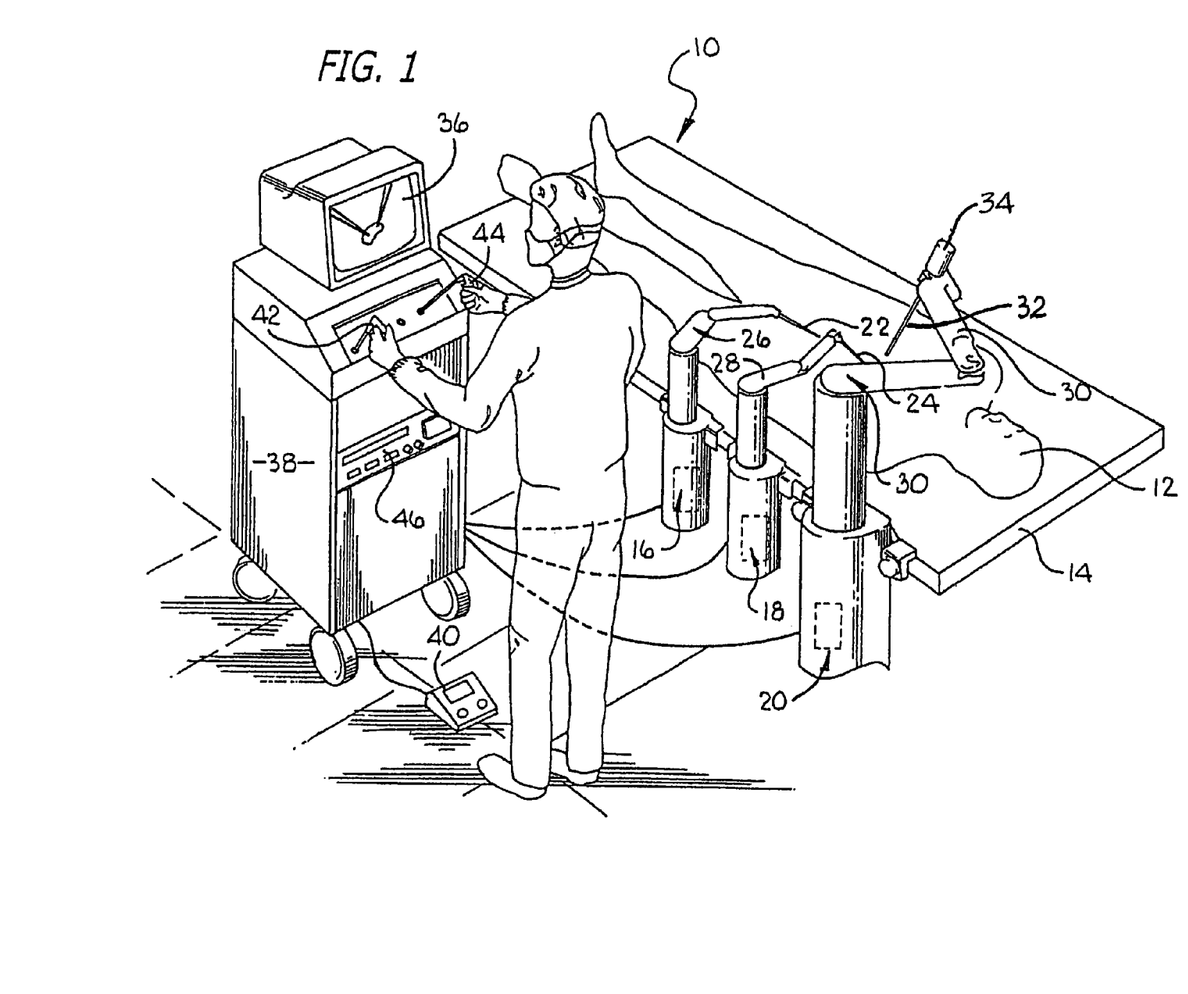
FIG. 1 is a perspective view of a medical robotic system.

Referring to the drawings more particularly by reference numbers, FIG. 1 shows a system 10 that can perform minimally invasive surgery. In one embodiment, the system 10 is used to perform a minimally invasive coronary artery bypass graft (MI-CABG) and other anastomostic procedures. Although a MI-CABG procedure is shown and described, it is to be understood that the system may be used for other surgical procedures. For example, the system can be used to suture any pair of vessels. The system 10 can be used to perform a procedure on a patient 12 that is typically lying on an operating table 14. Mounted to the operating table 14 is a first articulate arm 16, a second articulate arm 18 and a third articulate arm 20. The articulate arms 16, 18 and 20 are preferably mounted to the table 14 so that the arms are at a same reference plane as the patient. Although three articulate arms are shown and described, it is to be understood that the system may have any number of arms.

The first and second articulate arms 16 and 18 each have a surgical instrument 22 and 24, respectively, coupled to robotic arms 26 and 28, respectively. The third articulate arm 20 includes a robotic arm 30 that holds and moves an endoscope 32. The instruments 22 and 24, and endoscope 32 are inserted through incisions cut into the skin of the patient. The endoscope has a camera 34 that is coupled to a television monitor 36 which displays images of the internal organs of the patient.

The first 16, second 18, and third 20 articulate arms are coupled to a controller 38 which can control the movement of the arms. The controller 38 is connected to an input device 40 such as a foot pedal that can be operated by a surgeon to move the location of the endoscope 32. The controller 38 contains electrical circuits, such as a processor(s), memory, input/output drivers, etc. to control the robotic arms 26, 28 and 30. The surgeon can view a different portion of the patient by depressing a corresponding button(s) of the pedal 40. The controller 38 receives the input signal(s) from the foot pedal 40 and moves the robotic arm 30 and endoscope 32 in accordance with the input commands of the surgeon. The robotic arm may be a device that is sold by the assignee of the present invention, Computer Motion, Inc. of Goleta, Calif., under the trademark AESOP. The system is also described in U.S. Pat. No. 5,657,429 issued to Wang et al., which is hereby incorporated by reference. Although a foot pedal 40 is shown and described, it is to be understood that the system may have other input means such as a hand controller, or a speech recognition interface.

The robotic arms 26 and 28, and corresponding instruments 22 and 24, are controlled by a pair of master handles 42 and 44 that can be manipulated by the surgeon. The handles 42 and 44, and arms 16 and 18, have a master-slave relationship so that movement of the handles 42 and 44 produces a corresponding movement of the surgical instruments 22 and 24. The handles 42 and 44 may be mounted to a portable cabinet 46. The handles 42 and 44 are also coupled to the controller 38.

The controller 38 receives input signals from the handles 42 and 44, computes a corresponding movement of the surgical instruments, and provides output signals to move the robotic arms 26 and 28 and instruments 22 and 24. The entire system may be a product marketed by Computer Motion under the trademark ZEUS. The operation of the system is also described in U.S. Pat. No. 5,762,458 issued to Wang et al. and assigned to Computer Motion, which is hereby incorporated by reference.

Figure 2:
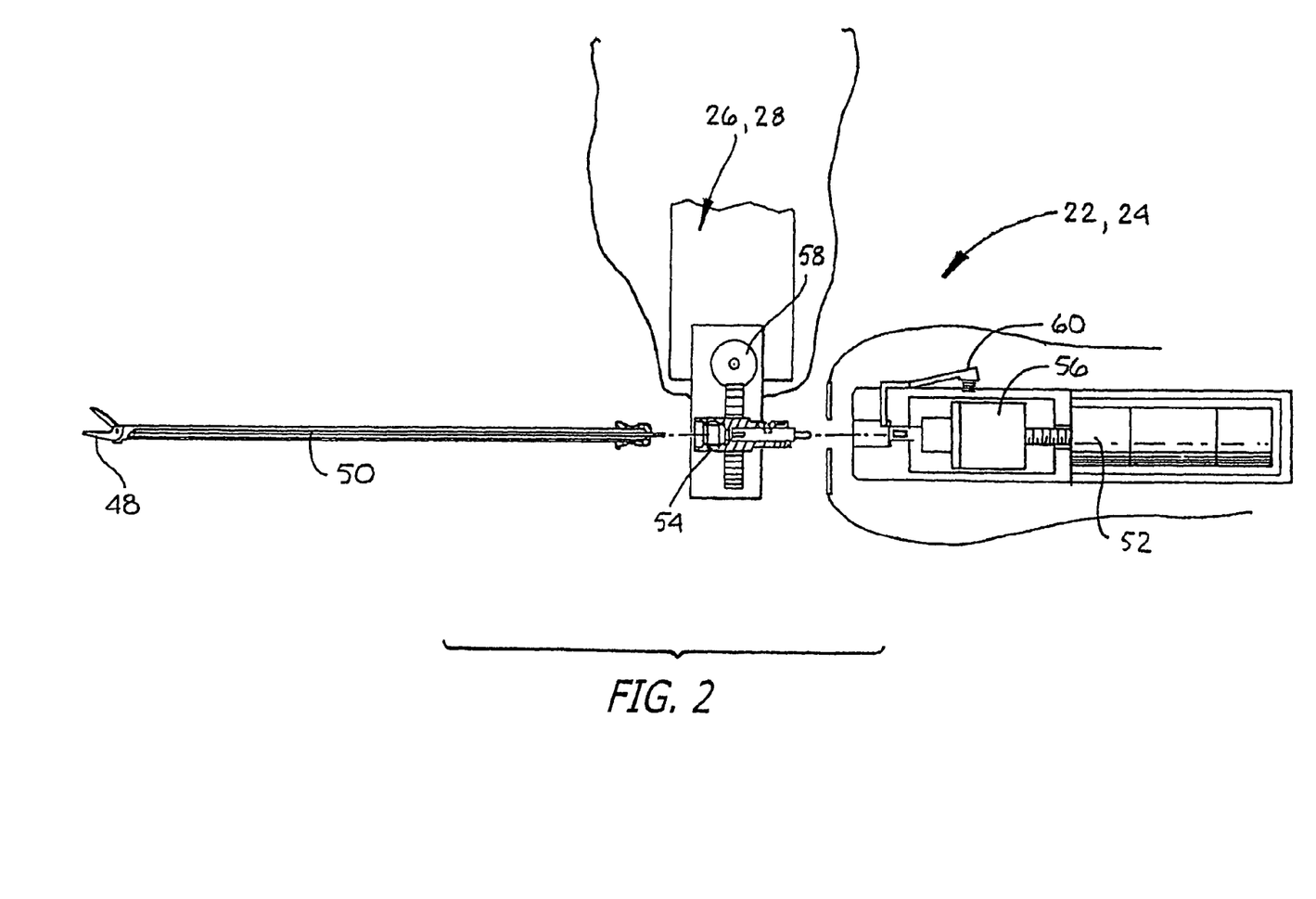
FIG. 2 is an exploded side view of an instrument of the robotic system.

FIG. 2 shows one of the surgical instruments 22 or 24. The instrument 22 or 24 includes an end effector 48 that is coupled to an actuator rod 50. The actuator rod 50 is coupled to a motor 52 by an adapter 54. The motor 52 actuates the end effector 48 by moving the actuator rod 50. The actuator rod 50 is coupled to a force sensor 56 that can sense the force being applied by the end effector 48. The force sensor 56 provides an analog output signal that is sent to the controller shown in FIG. 1. The force sensor can be used to provide force feedback on the handles 42 and 44 so that the surgeon "senses" the force exerted onto the end effector 50.

The adapter 54 is coupled to a gear assembly 58 located at the end of a robotic arm 26 or 28. The gear assembly 58 can rotate the adapter 54 and end effector 48. The actuator rod 50 and end effector 48 may be coupled to the force sensor 56 and motor 52 by a spring biased lever 60. The instrument 22 or 24 may be the same or similar to an instrument described in the '458 patent.

Figure 3:
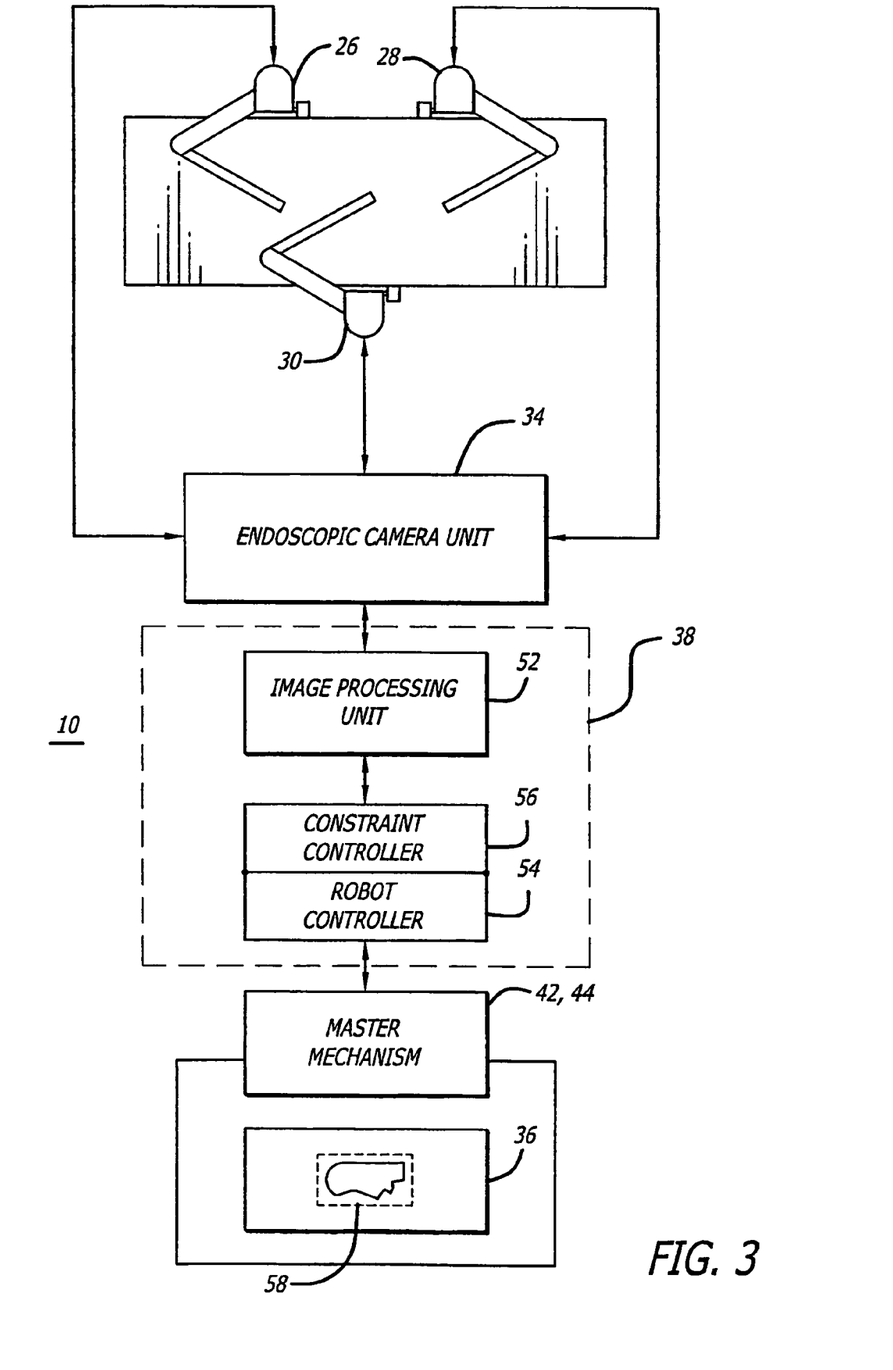
FIG. 3 is an illustration showing a system and a graphical constraint area defined on an image provided by the robotic system.

FIG. 3 shows a schematic of the robotic system 10. The controller 38 can be functionally separated into an image processing unit 52, a robot controller 54 and a constraint controller 56. The image processing unit 52 processes the image provided by the endoscope camera 34 for viewing on the monitor screen 36. The robot controller 54 converts movement of the handles 42, 44 and other input such as voice commands and/or depression of the foot pedal into corresponding movement of the robotic arms 26, 28 and 30. The robot controller 54 may utilize inverse kinematic equations to convert the input to movement of the robotic arms 26, 28 and 30. Examples of such equations can be found in both the '429 and '458 patents.

The constraint controller 56 constrains the movement of one or more of the robotic arms based on a predetermined parameter. By way of example, the parameter may be a surgical space 58 as shown in FIG. 3. The space can be defined as a point, a line, an area, or a volume.

The controller 56 may provide different modes of constraint. For example, the controller 56 may prevent a surgical instrument from entering the surgical space, or prevent the instrument from leaving the surgical space. The constraint may control the velocity of the instrument movement across the space, or provide damped movement into, or out of, the space.

Figure 4:
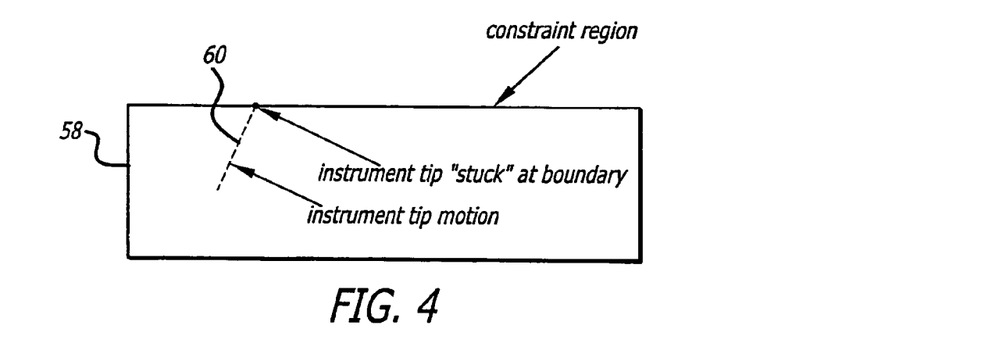
FIG. 4 is an illustration showing a sticking mode of constrained instrument movement.
Figure 5:
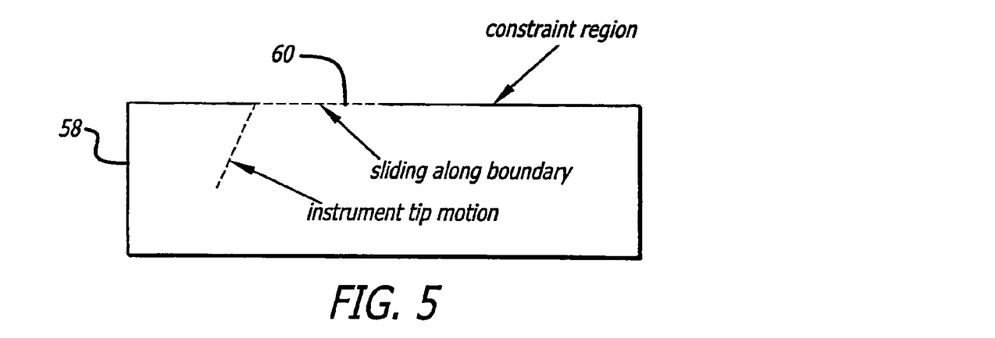
FIG. 5 is an illustration showing a sliding mode of constrained instrument movement.

FIG. 4 shows movement of an instrument tip 60 that cannot leave the constrained space 58. As the surgeon attempts to move the tip in a further upward direction, the constraint controller prevents such movement. As an alternative mode, the constraint controller may allow Movement along a boundary of the space as show in FIG. 5.

The handles 42, 44 may provide force feedback to the surgeon when the instrument reaches the boundary of a surgical space. The system may operate so that the handles 42 and 44 are prohibited from further movement when the instrument reaches the boundary. This may be utilized when the system is in the stick mode shown in FIG. 4. Conversely, the system may operate so that the surgeon can continue to move the handles 42 and 44 when the instrument reaches a boundary. This operation could be utilized in the sliding mode shown in FIG. 5.

The handles 42 and 44 may have two different types of mapping modes, relative and absolute mapping. In a relative mapping mode the instrument will automatically begin moving in a reverse direction when the handle movement is reversed. In an absolute mapping mode the handle must be moved back to the point where the instrument intersected the boundary before reverse instrument movement will follow the handle.

Figure 6:
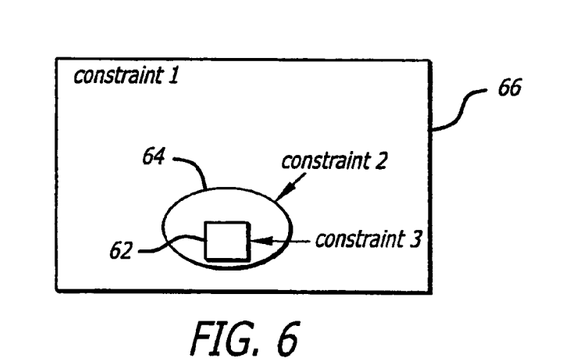
FIG. 6 is an illustration showing overlapping constrained surgical spaces.

FIG. 6 shows an embodiment wherein the constraint controller operates in accordance with a first predetermined parameter(s), a second predetermined parameter(s), a second predetermined parameter and a third parameter. The first parameter defines a first surgical space 62 that is located within a second space 64 defined by the second predetermined parameter(s). The first 62 and second spaces being located within a third space 64 defined by the third parameters (3). Each space may have a different constraint mode. For example, the instrument may be prevented from entering the first space 62, constrained from leaving the second space 64 and have a controlled velocity across the third space 66. An arbitrary number of spaces can be defined with one another.

Figure 7:
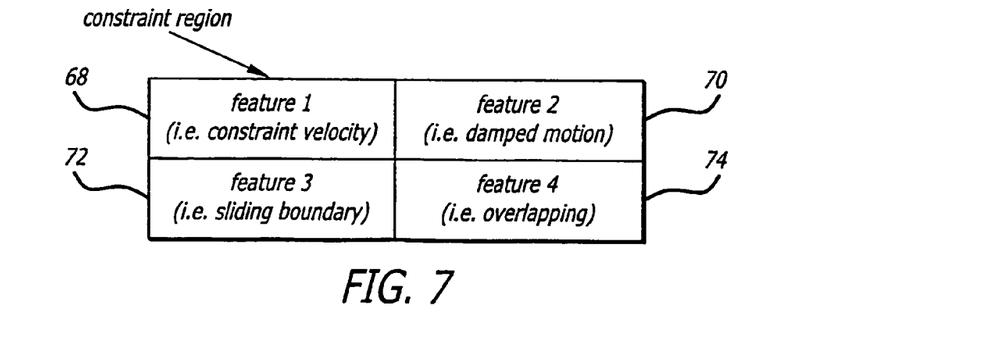
FIG. 7 is an illustration showing adjacent constrained surgical spaces.

FIG. 7 show as another embodiment wherein multiple adjacent spaces 68, 70, 72, and 74 can be created in the system. Each space 68, 70, 72, and 74 may have a different mode of constraint.

The boundaries of the space(s) can be created with a telestrator screen, wherein the operator utilized a pen to draw the boundaries over the video image of the patient. Other input modalities include voice commands, mouse and/or keyboard input.

Figure 8:
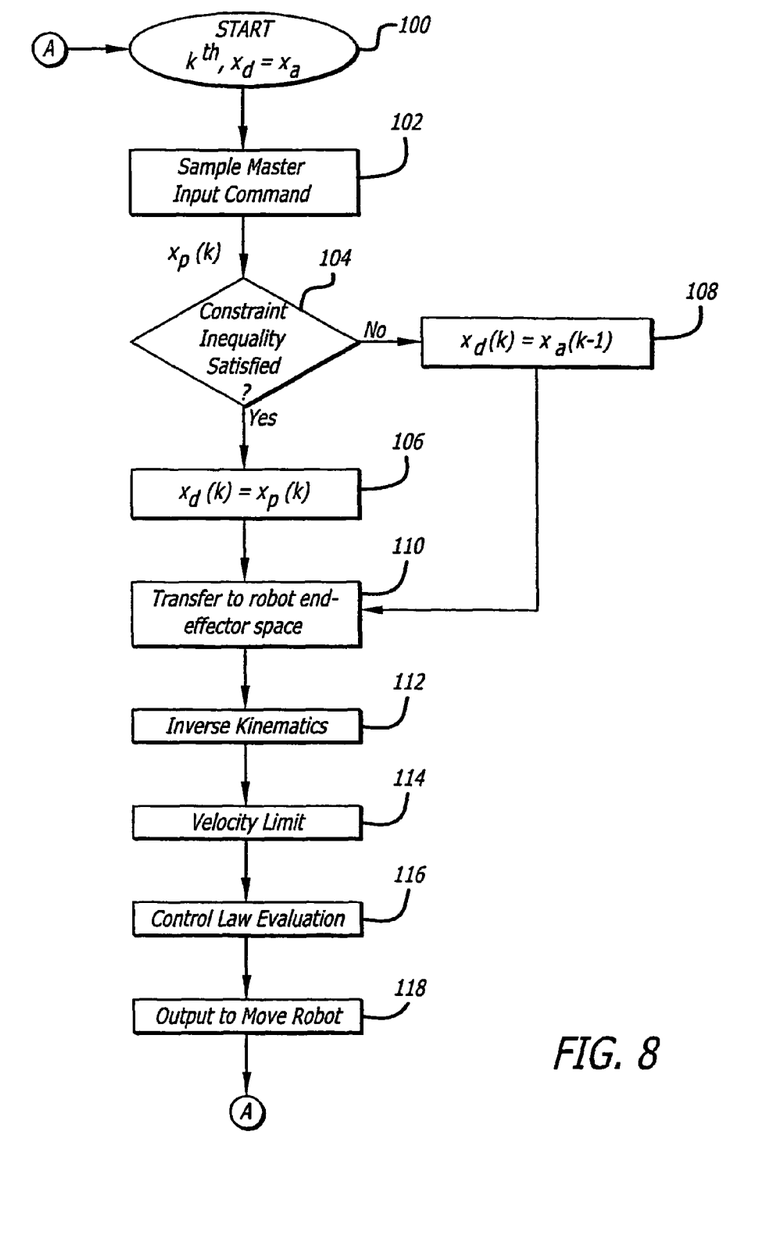
FIG. 8 is a flowchart for operation of a constraining function of the robotic system.

FIG. 8 shows a flowchart of constrained operation of the robotic system 10. At time step k the system starts with a desired instrument tip position $x_d$ equaling an actual instrument tip position $x_a$ in block 100. In block 102 the process samples an input command and provides a proposed new desired instrument tip position $x_p$. The process determines if the proposed position $x_p$ is equal to a constraint inequality in decision block 104. If the inequality. is satisfied the proposed position $x_p$ is set to the desired position $x_d$ in block 106. If the inequality is not satisfied the desired position $x_d$ is maintained at the prior actual position $x_a$ (k−1) in block 108.

In block 110 the desired position $x_d$ is transformed into the space of the end effector. The process utilizes inverse kinematics to transform the desired position $x_d$ into movement of the robotic arm in block 112. Velocity limits and control law evaluation is provided in blocks 114 and 116, respectively. The process then provides output signals to move the robotic arm in block 118. The process shown in FIG. 8 can be used to constrain the tip of an instrument.

Figure 9:
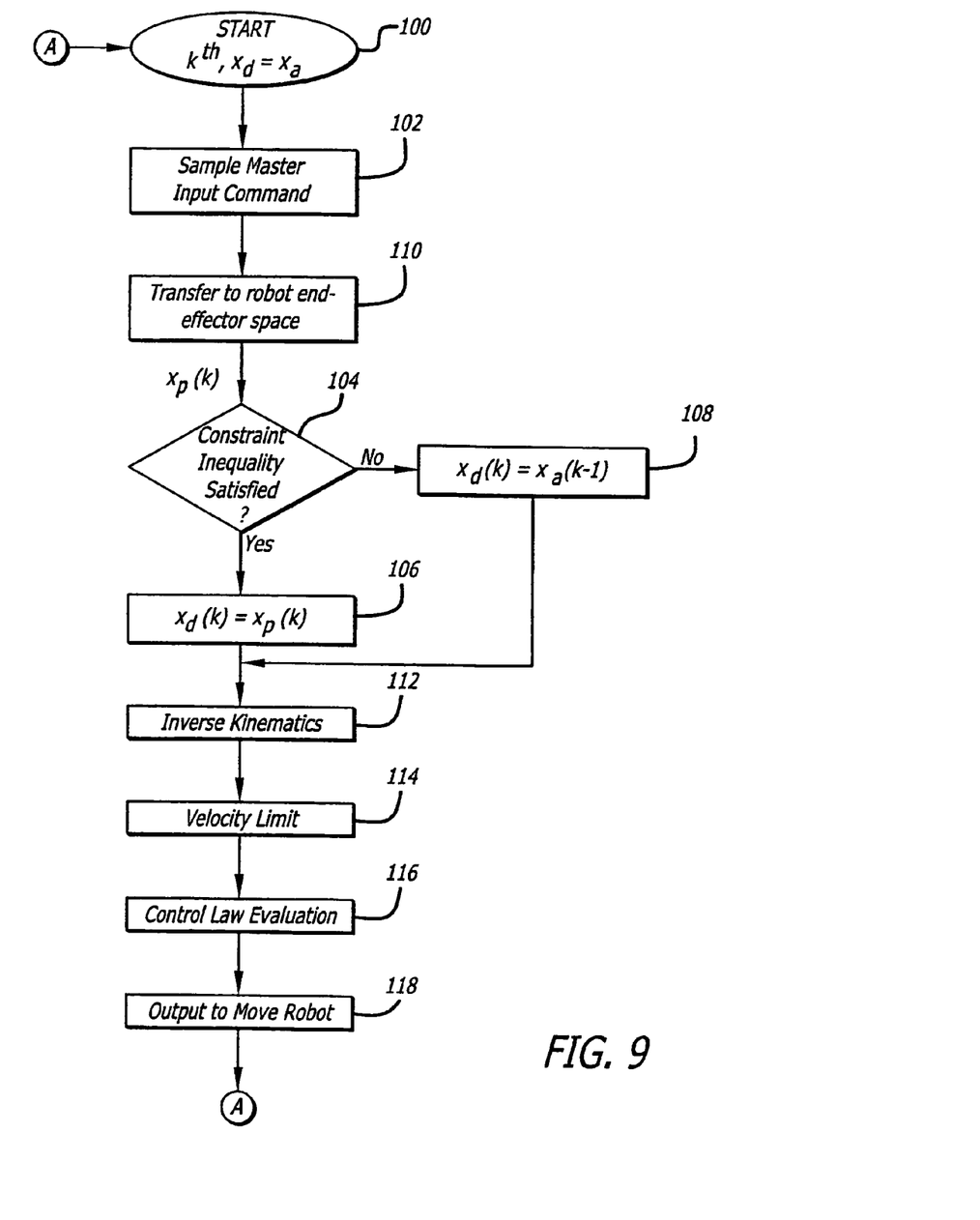
FIG. 9 is a flowchart for an alternative operation of a constraining function of the robotic system.

FIG. 9 shows a process used to constrain movement of the surgical instrument so that a vector of the instrument does not enter, or does not leave a surgical space. By way of example, such a process could insure that no part of the instrument enters a surgical space. The process is similar to the process of FIG. 9, except the transformation to the end effector space occurs before the constraint inequality is checked in decision block 104.

Figure 10:
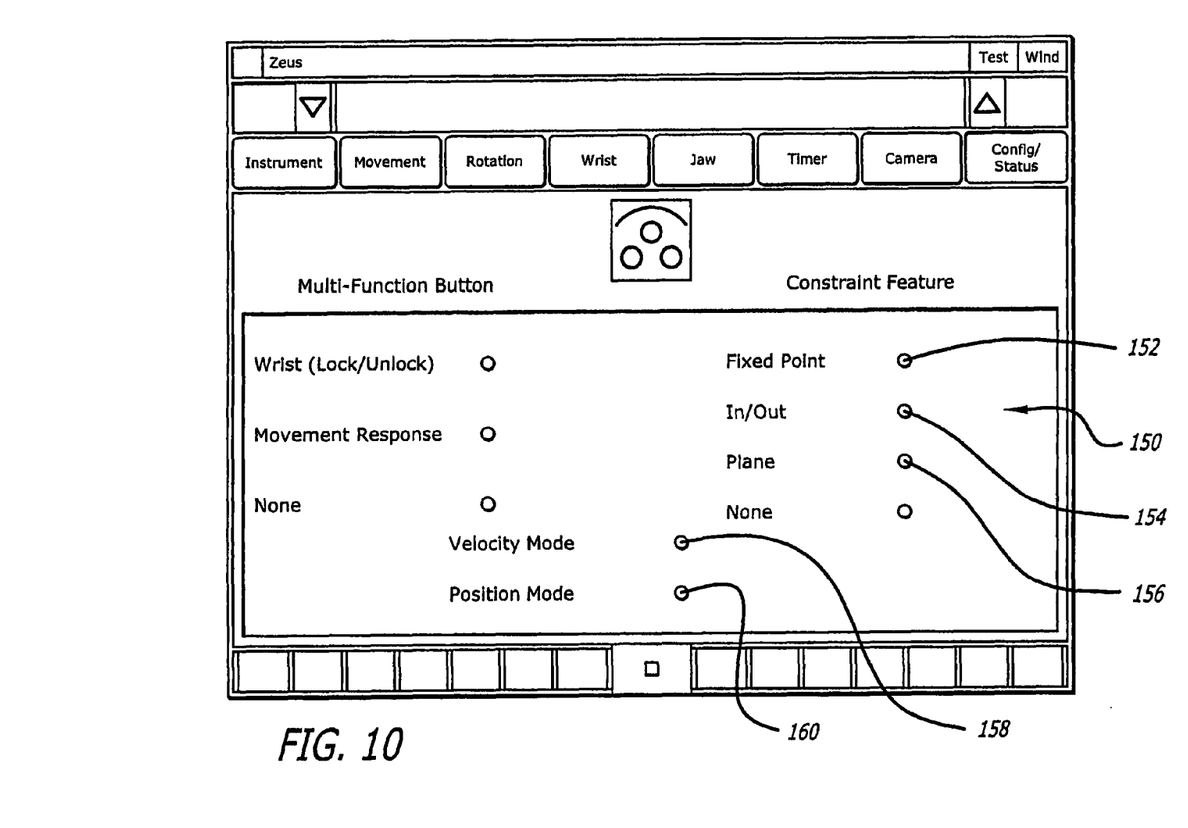
FIG. 10 is an illustration of a graphical user interface that can be used to enter constraint parameters.

FIG. 10 shows an embodiment of a graphical user interface 150 ("GUI") that can be used to input modes for the constraint parameters. The GUI 150 may include a fixed point button 152, In/Out button 154 and a plane button 156 to define the different types of surgical spaces. The GUI 150 may also have a velocity mode button 158 and a position mode button 160 to allow the surgeon to select a velocity constraint mode, or a position constraint mode, respectively.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

For example, although FIG. 3 schematically shows separate controllers 54 and 56, and processing unit 52, it is to be understood that the function provided by these controllers may be performed in accordance with instructions operated by one or more microprocessors.

What is claimed is:

1. A medical system comprising:
   an endoscope positioned to view a work site;
   a telestrator screen for displaying an image of the work site captured by the endoscope;
   a telestrator pen;
   a surgical instrument disposed at the work site for performing a procedure;
   a robotic arm adapted to hold and move the surgical instrument;
   a master handle; and
   a controller programmed with instructions to interpret a first telestration indicated by movement of the telestrator pen over the image of the work site being displayed on the telestrator screen as defining a first space within the work site, and to command the robotic arm to move the surgical instrument according to movement of the master handle and one or more constraint parameters that effect the commanded movement of the robotic arm differently as the surgical instrument moves into or moves within the first space than as the surgical instrument moves out of or moves outside of the first space.

2. The medical system according to claim 1, wherein the one or more constraint parameters is definable by the operator using a graphical user interface.

3. The medical system according to claim 1, wherein the one or more constraint parameters effect commanded movement of the robotic arm so as to prevent the surgical instrument from moving into the first space.

4. The medical system according to claim 1, wherein the one or more constraint parameters effect commanded movement of the robotic arm so as to prevent the surgical instrument from moving out of the first space.

5. The medical system according to claim 1, wherein the one or more constraint parameters effect commanded movement of the robotic arm so as to control the velocity of the surgical instrument.

6. The medical system according to claim 1, wherein the one or more constraint parameters effect commanded movement of the robotic arm so as to provide damped movement as the surgical instrument moves into the first space.

7. The medical system according to claim 1, wherein the one or more constraint parameters effect commanded movement of the robotic arm so as to provide damped movement as the surgical instrument moves out of the first space.

8. The medical system according to claim 1, wherein the controller is programmed with instructions to interpret a second telestration indicated by movement of the telestrator pen over the image of the work site being displayed on the telestrator screen as defining a second space within the work site, and to command the robotic arm to move the surgical instrument according to movement of the master handle and one or more second constraint parameters that effect the commanded movement of the robotic arm differently as the surgical instrument moves into or moves within the second space than as the surgical instrument moves out of or moves outside of the second space.

9. The medical system according to claim 8, wherein the second space is completely within the first space and the one or more second constraint parameters effect commanded movement of the robotic arm so as to prevent the surgical instrument from moving out of the first space and into the second space.

10. A medical system comprising:
    an endoscope positioned to view a work site;
    a telestrator screen for displaying an image of the work site captured by the endoscope;
    a telestrator pen;
    a surgical instrument disposed at the work site for performing a procedure;
    a robotic arm adapted to hold and move the surgical instrument;
    a master handle; and
    a processor programmed with instructions to interpret a first telestration indicated by movement of the telestrator pen over the image of the work site being displayed on the telestrator screen as defining a boundary within the work site, to receive a proposed new position of the surgical instrument as commanded by movement of the master handle, to determine whether the proposed new position satisfies an inequality defined by the boundary, and to command the robotic arm to move the surgical instrument to a desired position of the surgical instrument, wherein the desired position of the surgical instrument is set to the proposed new position of the surgical instrument if the inequality is satisfied, and wherein the desired position of the surgical instrument is maintained at a current position of the surgical instrument if the inequality is not satisfied.

11. A method for controlling movement of a surgical instrument in response to operator manipulation of a master handle, comprising:
    using a processor to interpret a first telestration indicated by movement of a telestrator pen over an image of a work site being displayed on a telestrator screen as defining a first work space within the work site; and
    using the processor to command a robotic arm to move the surgical instrument according to operator manipulation of the master handle and one or more constraint parameters that effect the commanded movement of the robotic arm differently as the surgical instrument moves into or moves within the first space than as the surgical instrument moves out of or moves outside of the first space.

12. The method according to claim 11, further comprising: providing the one or more constraint parameters to the processor from a graphical user interface.

13. The method according to claim 11, wherein the one or more constraint parameters effect the commanded movement of the robotic arm so as to prevent the surgical instrument from moving into the first space.

14. The method according to claim 11, wherein the one or more constraint parameters effect the commanded movement of the robotic arm so as to prevent the surgical instrument from moving out of the first space.

15. The method according to claim 11, wherein the one or more constraint parameters effect the commanded movement of the robotic arm so as to control the velocity of the surgical instrument.

16. The method according to claim 11, wherein the one or more constraint parameters effect the commanded movement of the robotic arm so as to provide damped movement as the surgical instrument moves into the first space.

17. The method according to claim 11, wherein the one or more constraint parameters effect the commanded movement of the robotic arm so as to provide damped movement as the surgical instrument moves out of the first space.

18. The method according to claim 11, further comprising:

using the processor to interpret a second telestration indicated by movement of the telestrator pen over the image of the work site being displayed on the telestrator screen as defining a second space within the work site;

wherein using the processor to command the robotic arm to move the surgical instrument includes using the processor to command the robotic arm to move the surgical instrument according to one or more second constraint parameters that effect the commanded movement of the robotic arm differently as the surgical instrument moves into or moves within the second space than as the surgical instrument moves out of or moves outside of the second space.

19. The method according to claim 18, wherein the second space is completely within the first space and the one or more second constraint parameters effect the commanded movement of the robotic arm so as to prevent the surgical instrument from moving out of the first space and into the second space.

* * * * *